United States Patent
O'Donnell et al.

(10) Patent No.: US 6,254,569 B1
(45) Date of Patent: *Jul. 3, 2001

(54) AUTOMATIC ENGAGEMENT AND PRESSURE CHECKING SYSTEM FOR AN INFLATION CONTROL SYSTEM

(75) Inventors: Joseph A. O'Donnell, Escondido; Steven D. Royce, San Diego; Albert A. Quinones, Murrieta, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/406,025

(22) Filed: Mar. 17, 1995

(51) Int. Cl.$^7$ .................................................. A61M 29/00
(52) U.S. Cl. ............................................................ 604/97
(58) Field of Search ........................ 604/99, 100, 30–34, 604/65, 66, 67, 118, 97; 128/DIG. 1, DIG. 12, DIG. 13

(56) References Cited

U.S. PATENT DOCUMENTS

| | | | |
|---|---|---|---|
| 4,106,002 | 8/1978 | Hogue, Jr. ............................. | 340/626 |
| 4,677,980 | * 7/1987 | Reilly et al. ..................... | 128/DIG. 1 |
| 4,694,409 | 9/1987 | Lehman ................................ | 364/558 |
| 5,152,776 | * 10/1992 | Pinchuk .................................. | 604/97 |
| 5,459,700 | * 10/1995 | Jacobs .................................. | 604/100 |
| 5,520,653 | * 5/1996 | Reilly et al. ..................... | 128/DIG. 1 |

OTHER PUBLICATIONS

U.S. application No. 08/406,040, Lawrence et al., filed Mar. 17, 1995, pending.

* cited by examiner

*Primary Examiner*—Manuel Mendez
(74) *Attorney, Agent, or Firm*—Fulwider Patton Lee & Utecht, LLP

(57) ABSTRACT

An automated engagement system for coupling the plunger of a syringe to a drive arm is provided. A pressure integrity test of the syringe assembly is automatically conducted after engagement. After a position sensor communicates a signal indicating the presence of a properly installed syringe assembly to a processor, a display prompts the operator to vent and then close a stopcock in the fluid line. The processor then controls the drive arm of the system to move into engagement with the plunger of the syringe assembly, and to move the plunger forward into the syringe barrel. The drive arm stops when a pressure sensor produces a signal indicating a positive pressure in the fluid line. The processor then controls the drive arm to move the plunger in a reverse direction until a negative pressure is detected. After this confirmation of pressure integrity in the syringe assembly, the processor controls the drive to move forward until a non-negative pressure is detected by the pressure sensor.

12 Claims, 11 Drawing Sheets

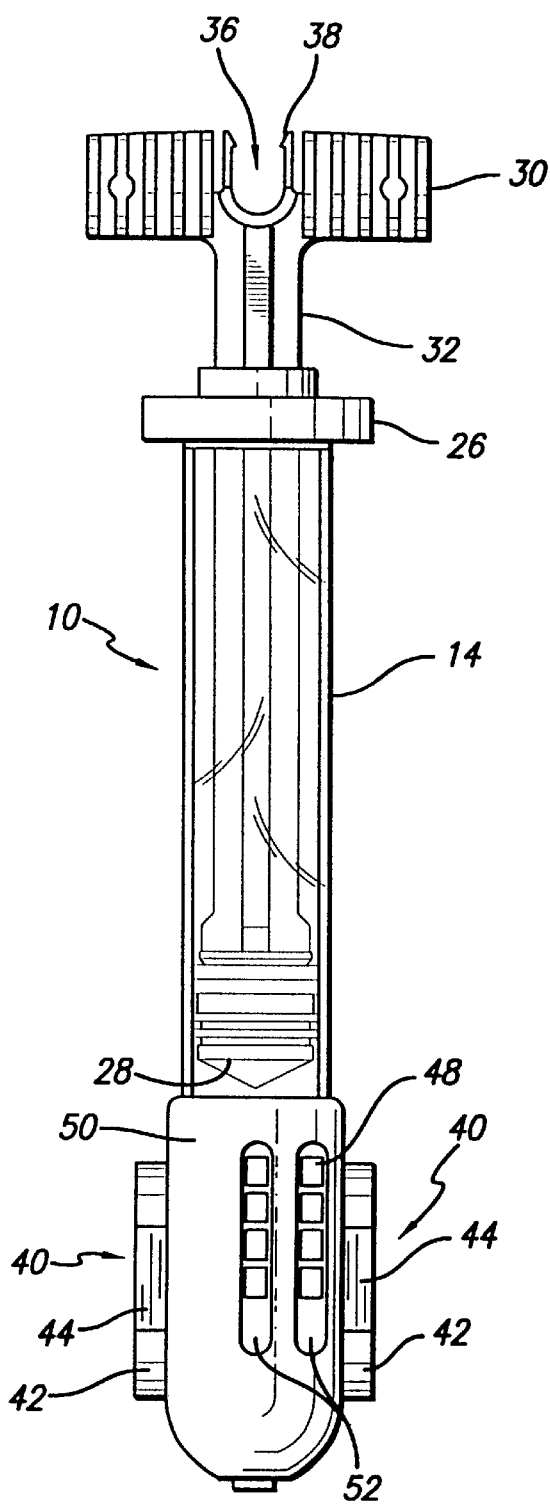
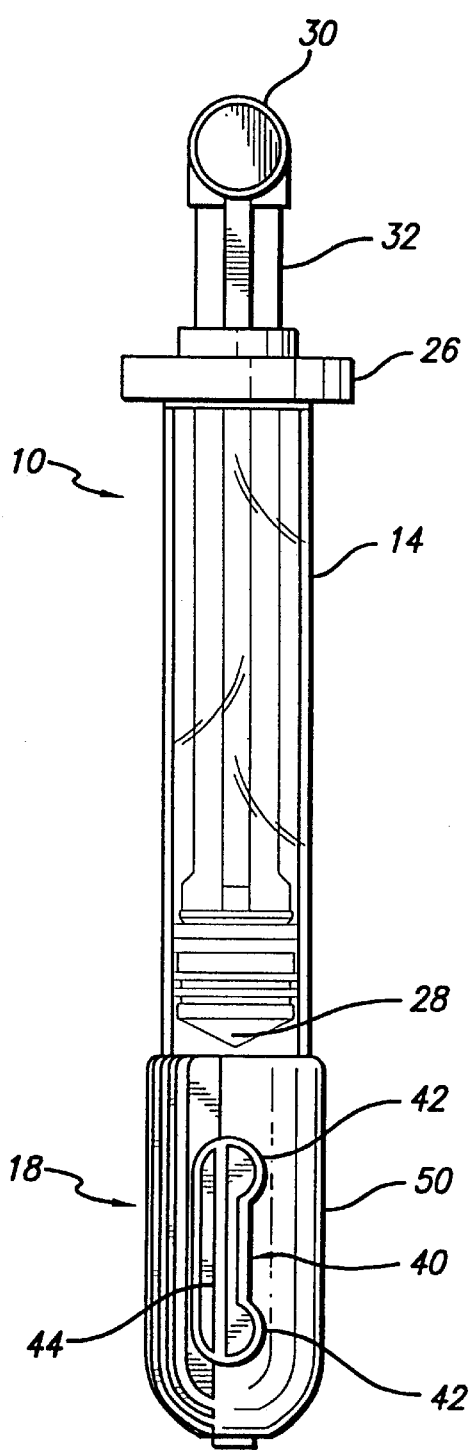
FIG. 2
FIG. 3

AUTOMATIC ENGAGEMENT AND PRESSURE CHECKING SYSTEM FOR AN INFLATION CONTROL SYSTEM

BACKGROUND

The invention generally relates to inflation devices used in medical procedures, and more particularly, to inflation control systems suitable for controlling the inflation and deflation of balloons or other inflatable devices used in medical procedures, such as balloon catheters used in angioplasty procedures.

Dilatation balloon catheters have been used in increasing numbers in angioplasty procedures to dilate or enlarge blood vessels that have been partially or almost completely blocked by stenosis (a narrowing of the vessel due to injury or disease). Angioplasty procedures have been used to treat stenoses in coronary arteries, peripheral arteries, urethral passages, fallopian tubes, etc. Particularly, the procedure for dilating coronary arteries, referred to as percutaneous transluminal coronary angioplasty (PTCA), has provided an effective and less traumatic treatment technique than coronary by-pass surgery or other surgical treatment methods.

In a typical angioplasty procedure, a guiding catheter is percutaneously introduced into the vascular system of a patient and is directed to a point near the site of the stenosis. Subsequently, a guidewire and a dilatation catheter having an inflatable balloon mounted on the distal end thereof are introduced through the guiding catheter with the guidewire slidably disposed within an inner lumen of the dilatation catheter. The guidewire is advanced out of the distal end of the guiding catheter and is maneuvered into the patient's vasculature containing the stenosis to be dilated, and is then advanced beyond the stenosis. Thereafter, the dilatation catheter is advanced over the guidewire until the dilatation balloon is located across the stenosis. Once in position, the dilatation balloon is inflated to a predetermined size, typically the same size as the inner diameter of the blood vessel at that location, by radiopaque liquid at relatively high pressures (e.g., generally greater than about four atmospheres). The inflated, pressurized balloon radially compresses the atherosclerotic plaque of the stenosis against the inside of the vessel wall to thereby dilate the lumen of the vessel and allow increased blood flow through the vessel.

In a typical PTCA procedure, the balloon is inflated and deflated several times with the pressure maintained for several seconds during each inflation, until the desired patency in the blood vessel is obtained. The physician typically monitors a timing device to control the duration of each inflation and the duration between inflations. Each inflation of the balloon interferes with the blood supply circulation; therefore, the duration must be kept as short as possible, yet must still be long enough to obtain the results desired. The duration between inflations is monitored to allow enough time for the blood supply to reestablish itself before the next inflation. After the procedure has been completed, the balloon is deflated for the final time and maintained under negative pressure so that the dilatation catheter can be withdrawn from the patient and the blood flow resumed through the dilated vessel.

To inflate or deflate the balloon, the physician typically uses an inflation device, such as a syringe, placed in fluid communication with the interior of the balloon. The physician uses one hand to grasp the syringe body and the other hand to maneuver the plunger to pressurize or depressurize the inflation fluid as required. Manually operated syringe-type inflation systems of the type described are manufactured and sold by Advanced Cardiovascular Systems, Inc. of Santa Clara, Calif. under the trademark INDEFLATOR.

Such manual inflation systems have proven to be of great value in conducting angioplasty procedures. Some systems include a pressure sensor with a display that indicates to the operator the fluid pressure in the catheter/balloon. A balloon pressure display allows the physician to monitor whether the arterial plaque causing the stenosis is subjected to a sufficiently high pressure to cause compression of the plaque. Such a display also allows the physician to monitor the pressure to ensure that the balloon pressure limits specified by the manufacturer are not exceeded. Furthermore, if the pressure display indicates a sudden and unexpected decrease in pressure, the physician may be alerted so that any necessary remedial action can be taken.

However, manual systems typically require the physician to use both hands to control the inflation and deflation processes. Each time an adjustment in the location of the balloon in the patient's vessel must be made, the physician must move at least one hand from the inflation control system to the catheter to accomplish the relocation of the balloon, and must then return to the inflation system with both hands. Rather than having to use both hands on the inflation device, it would be preferable for the physician to only use one hand thereby leaving the second hand free to control the position of the catheter in the vessel or to perform other tasks, as needed.

A further consideration with manual inflation systems is the ease with which the system can be used. In manual systems that require a substantial amount of hand strength to maneuver the syringe plunger for developing enough pressure in the balloon to compress the plaque, the physician may experience hand fatigue as a result of operating such an inflation device for several inflation and deflation cycles, each lasting several seconds.

Inflation control systems using a motor drive to control the position of a plunger in a syringe to control the balloon pressure have been described. Such motor drive inflation systems reduce or eliminate the need for the physician to manually control the position of the plunger in the syringe. The physician instead controls the movement of a motor through an electrical switch. That motor performs the work of moving the syringe plunger. Usually only one hand is needed to operate the electrical switch or switches needed for motor control thus leaving one of the physician's hands free to locate the catheter or perform other tasks. Such systems can provide the ability to inflate or deflate the balloon catheter at a precise moment during the maneuvering of the catheter in the patient's vessel with relatively precise control over the rates of inflation and deflation.

Motor driven inflation systems typically use a syringe or syringe-type fluid reservoir for containing the fluid that is to be pressurized to control balloon inflation. Typically, the syringe comprises a barrel with a movable plunger to control the volume in the barrel thereby controlling the pressure developed. At the far end of the barrel, a smaller diameter nozzle is used to make fluid communication with a fluid line. The fluid line is connected to the dilatation catheter at the start of the procedure. However prior to that time, the syringe assembly must be prepared for use.

Typically, the syringe assembly is provided empty. That is, no radiopaque fluid is present in the barrel of the syringe. The operator would usually remove the syringe assembly from its packaging, immerse the fluid line in the fluid to be used for the angioplasty procedure, and draw some of that fluid into the fluid line and syringe barrel. Air would then be expelled. To accomplish this preparation, a stopcock is provided at the distal end of the fluid tubing. The stopcock has three positions. The first of closed, the second is open to a connected catheter, and the third is vent to atmosphere. Thus the syringe assembly has three main components: a syringe, a fluid tubing, and a stopcock.

After the syringe assembly has been fully prepared, it is then mounted to the motor drive instrument and the plunger is engaged with the drive mechanism. In some prior cases, this engagement procedure can require the manipulation of mechanical devices by the instrument operator to connect the drive device to the plunger so that the plunger's position will be under motor control. The manipulation of complex devices to achieve engagement or the requirement of significant strength to manipulate those devices are both undesirable. It is desirable that the engagement process be straight forward and require little effort on the part of the operating personnel. After engagement has been effected, the syringe is connected to the dilatation catheter by means of a luer connector and the stopcock opened for fluid communication with the catheter.

Relatively high pressures are developed in dilatation procedures, in some cases, over ten atmospheres. Additionally, negative pressure must be drawn in the syringe assembly to assure collapse of the dilatation balloon for withdrawal from the patient. Thus, the syringe assembly must be capable of withstanding these high positive pressures and negative pressures. Should the syringe, tubing, or stopcock have a pressure leak and be unable to develop ten atmospheres of pressure during a procedure, the physician may be forced to replace the syringe assembly with another during the procedure. This would require preparing the new syringe assembly, including drawing fluid into the syringe, and the expulsion of any air trapped in the new syringe. The removal of the old assembly, the preparation of the new assembly and its mounting to the instrument can undesirably delay the dilatation procedure.

Prior to commencement of the angioplasty procedure, it would be useful to determine whether the selected syringe assembly can support the pressures required during the procedure. If a syringe assembly unable to support these pressures could be identified prior to the start of the procedure, it could be replaced at that time rather than during the procedure.

Hence those skilled in the art have recognized the need for an engagement system for mating a drive device with the syringe plunger of a syringe that is relatively simple and easy to operate. Also, those skilled in the art have recognized the need for an automated pressure integrity check of a syringe before a dilatation procedure begins so that the ability to reach the desired pressures during a medical procedure can be verified before the procedure is begun. The present invention fulfills these needs and others.

SUMMARY OF THE INVENTION

The invention is directed to an inflation control system for the automatic engagement of a pressure control device with a movable driver. In a further aspect, the invention is directed to the automatic performance of a pressure integrity test of a mounted pressure control device.

In more detailed aspects, an inflation control system is provided that comprises a movable driver that moves in longitudinal directions in response to drive signals and a syringe assembly that comprises a syringe barrel having a volume and a plunger opening at a proximal end and an output at a distal end, a fluid tube in fluid communication with the barrel volume through the output, a plunger movably disposed in the plunger opening and in the barrel for altering the volume by means of its position in the barrel, the plunger having a driver retainer at a proximal end, the retainer permitting the driver to automatically engage the retainer from one direction and after engaging, securing the plunger to the driver so that the plunger moves with the driver in longitudinal directions, and a pressure sensor producing a signal representative of the pressure within said tube. A mounting bracket is provided for engaging the syringe assembly and for maintaining said syringe assembly in a stationary position in relation to the driver. Furthermore, a processor provides drive signals to the movable driver to automatically move the driver into engagement with the plunger retainer.

In a further feature, the processor provides drive signals to a drive device to perform a syringe pressure integrity test after engagement of a drive arm of the drive device with the driver retainer. In more detail, after the processor has moved the drive arm into engagement with the driver retainer, the processor controls the drive device to move the drive arm in a first longitudinal direction until a positive pressure is sensed by the pressure sensor and in a second longitudinal direction until a negative pressure is sensed by the pressure sensor.

In yet further aspects, a flow control device is adapted to close the fluid line, wherein the processor provides drive signals to the drive device to perform a syringe pressure integrity test after engagement of the drive arm with the plunger retainer, and after the processor has moved the drive arm into engagement with the plunger retainer, the processor controls the drive device to move the drive arm in a first longitudinal direction until a positive pressure is sensed by the pressure sensor and in a second longitudinal direction until a negative pressure is sensed by the pressure sensor.

In further detailed aspects in accordance with the invention, a flow control device is adapted to open the fluid line and the processor receives the pressure sensor signal, compares it to a predetermined range of pressures and indicates an alarm if the sensor signal is outside that range.

In detailed aspects concerning the driver retainer, the drive arm comprises resilient retainer prongs that spread apart when initially contacted by the drive arm and which return to their at-rest positions when fully engaged by the drive arm to capture the drive arm between them. Furthermore, a notch is formed in said drive arm, and at least one of said at least two retainer prongs includes a barb for engaging said notch.

In yet a further detailed aspect, a syringe insertion detector produces an insertion signal indicating when said syringe is properly mounted, wherein the processor enables the pressure verification test after receipt of the insertion signal.

These and other advantages of the invention will become more apparent from the following detailed description thereof when taken in conjunction with the accompanying exemplary drawings.

BRIEF DESCRIPTION OF THE DRAWINGS

FIG. 2 is a top view of the syringe and pressure sensor of the syringe assembly of FIG. 1;

FIG. 3 is a side view of the syringe and pressure sensor of the syringe assembly of FIG. 1;

DETAILED DESCRIPTION OF THE PREFERRED EMBODIMENTS

Figure 1:
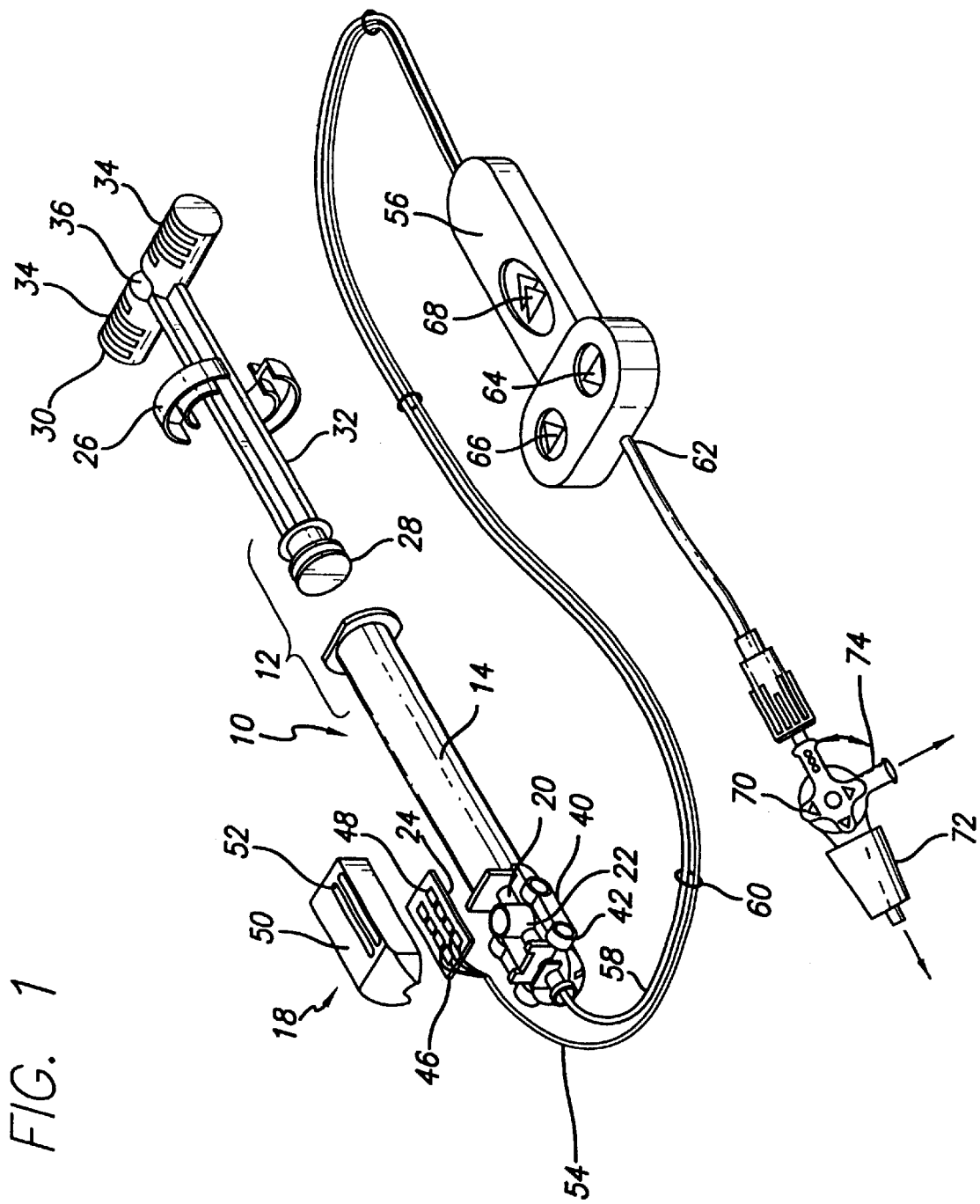
FIG. 1 is a partially exploded view of a syringe assembly having a syringe, fluid tubing, and a pressure sensor mounted to the fluid tubing to sense the fluid pressure in that tubing.

Referring now to the drawings in which like reference numerals designate like or corresponding features among the several views, FIGS. 1 through 3 illustrate a syringe assembly 10 that includes a syringe 12 having a syringe barrel 14, or other fluid chamber, and a plunger 16 disposed at one end of the syringe barrel 14 for altering the volume in the syringe barrel depending on the position of the plunger 16 in the barrel 14. The syringe assembly also includes a mounting head 18 disposed at the opposite or distal end of the syringe barrel from the plunger. Rigid fluid tubing 20 is coupled to the distal opening in the barrel for conducting inflation fluid to and from the syringe barrel. The rigid tubing 20 provides fluid communication with a downstream flexible tubing 58 which may be made of any suitable material that can withstand the pressures associated with the inflation and deflation of a balloon catheter, or other inflatable device. The preferred material suitable for the flexible tubing 58 is polyurethane with a braided nylon. Other possible materials are PVC or flexible copolymers.

A sensor port 22 and a pressure sensor 24 are mounted to the fluid tubing 20. The sensor port is in fluid communication with the fluid tubing and therefore the pressure sensor provides an indication of the fluid pressure in the fluid tubing 20. The pressure sensor 24 can be a strain beam type sensor or a piezo-resistive transducer or other types.

The plunger 16 includes a plunger retainer 26 that maintains the plunger at a selected orientation within the syringe barrel 14. The plunger further includes a movable piston 28 that controls the volume in the syringe barrel 14. Moving the piston distally decreases the volume in the syringe barrel and in a closed system, increases the pressure. Moving the piston proximally increases the volume in the syringe barrel and decreases the pressure in a closed system. A plunger handle 30 is connected to the piston through the plunger shaft 32. Movement of the handle causes respective movement of the piston in the barrel.

The plunger handle 30 includes two generally rounded lateral extensions 34 extending in opposite directions from the plunger shaft 32 to form a "T" shape. As will be described in more detail below, the rounded shape of these extensions facilitates grasping the handle by an operator to disengage the syringe assembly from the mounting and driving system for manual control. A driver retainer 36 is located between the two extensions 34 of the handle 30 and is aligned with the longitudinal axis of the shaft 32. The driver retainer 36 includes two parallel prongs 37 extending proximally, each prong having a barb 38 disposed at its farthest end on the inside surface. The two parallel prongs of the driver retainer 36 define a space therebetween for accepting a drive arm that controls the position of the syringe plunger 16.

The mounting head 18 is fixedly mounted to the distal end of the syringe barrel 14 and includes a pair of rounded projections 40 located laterally on either side in respect to the syringe barrel 14. These projections 40 are shaped and sized to provide pivotal mounting for the syringe assembly in a mounting bracket as is shown and described in greater detail below. Each projection 40 as shown comprises two rounded ends 42 or ears with a connecting ridge 44 between them. The pivotal mounting arrangement with the pivot being located at one end of the syringe assembly, and the point of force being applied at the other end of the assembly provides greater mechanical advantage to one attempting to remove the syringe assembly 10 from the mounting structure. While the drawings show the embodiment where the mounting head 18 and the rounded mounting projections 40 are attached to the distal end of the syringe barrel, other embodiments are possible. For example, the projections may be formed as part of the syringe barrel in another configuration.

The mounting head 18 includes a circuit board 46 having open contact surfaces 48 for establishing an electrical connection between circuits in an instrument and circuits in the syringe assembly 10. One circuit in the syringe assembly is the pressure sensor 24 and in this embodiment, the pressure sensor comprises a strain beam type or piezo-resistive type sensor. The circuit board 46 has eight contact surfaces 48 although more or fewer may be required depending on the circuits contained in the syringe assembly 10. In this case, the syringe assembly includes the pressure sensor 24 and the electrical leads for a remote controller 56. A cover 50 protects the board 46 from damage. The cover 50 includes two slots 52 to permit access to the contact surfaces 48 of the circuit board 46.

The circuit board 46 includes lead wires 54 that form an electrical connection with the remote controller 56. The rigid fluid line 20 is in fluid communication with a flexible fluid line 58 that also leads to the remote controller 56 in FIG. 1. The lead wires 54 and flexible fluid line 58 are kept bundled together by a plurality of elastic bands 60. The electrical lead wires 54 terminate in the remote controller 56 while the fluid line 58 travels beyond the remote controller for eventual connection to a catheter (not shown). A slot 62 is formed in the bottom surface of the remote controller 56 along its length and the flexible fluid line 58 is mounted in that slot. The slot 62 is slightly smaller than the flexible tubing 58 and is deep enough so that once inserted, the flexible tubing tends to remain in the slot. This and the banding of the electrical lead wires with the flexible tubing have the advantageous effect of reducing the clutter by retaining the devices together.

The remote controller 56 can be operated either by the physician who also is maneuvering the proximal end of the balloon catheter as well as by an assistant who may stand near the physician without interfering with the physician's handling of the proximal end of the balloon catheter. In this case, the flexible tubing 58 would be pulled out of the slot 62 to separate it from the controller and the bands 60 moved toward the syringe assembly so that the controller 56 can be operated by the assistant while the catheter can be operated by the physician. This separated configuration is shown in FIG. 6.

The remote controller 56 includes a plurality of switches. These switches may be rocker switches, slide switches, rotary switches, non-electrical pneumatic control switches, any other types or combinations of switches for providing control signals. In this embodiment, dome switches that click when depressed have been used. In addition to clicking audibly, these switches provide a mechanical feel of a click when depressed.

Figure 6:
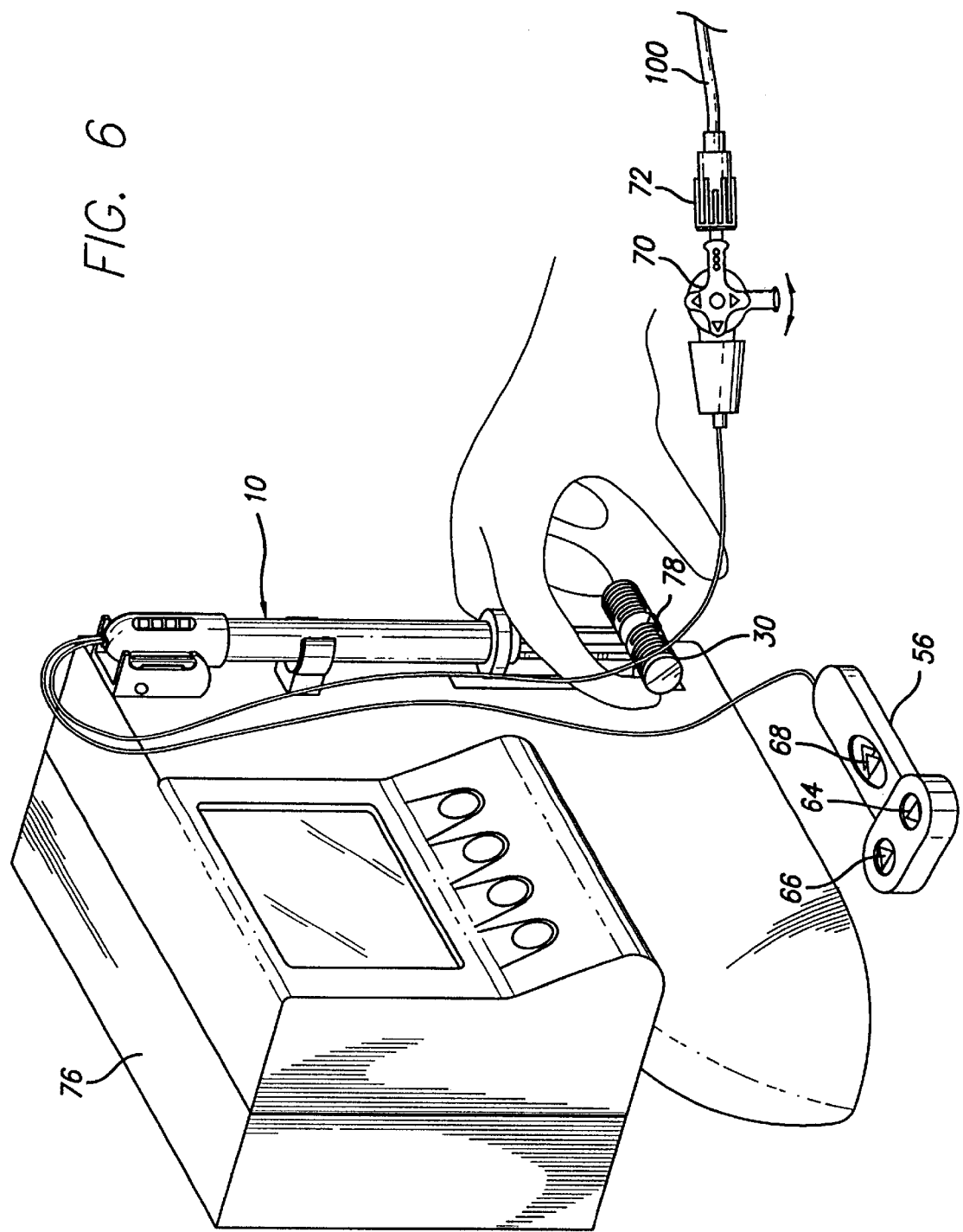
FIG. 6 shows the syringe assembly of FIG. 1 installed in the mounting bracket and clamp on the instrument and a technique for rapidly removing the syringe assembly from its mounted position.

The three switches of the remote controller 56 shown in FIG. 6 comprise an increase-pressure switch 64, a decrease-pressure switch 66, and a rapid-decrease-pressure switch 68. Should rapid deflation of the balloon be desired, the rapid decrease-pressure switch 68 may be activated to rapidly decrease the pressure in an inflatable device to a predetermined level, in this embodiment to a partial vacuum of −7 psi.

A stopcock 70, or other suitable fluid control device, is located at the distal end of the flexible fluid line 58 and is secured to the fluid line by a rotating luer lock connector 72.

The stopcock 64 controls the fluid communication of the fluid line 58. Three positions are available in this case. The first position as shown in FIG. 1 closes the fluid line so no fluid communication with any external device or line can occur. the second position vents the fluid line 58 to outside air through a vent port 74, and the third position will establish fluid communication between the fluid line 58 and a connected catheter (not shown). When the stopcock is placed in the third position, the syringe assembly 10 then will control the pressure in the catheter based on the volume of the syringe barrel. Stopcocks and luer connectors are well known to those skilled in the art and no further details are provided.

Figure 4:
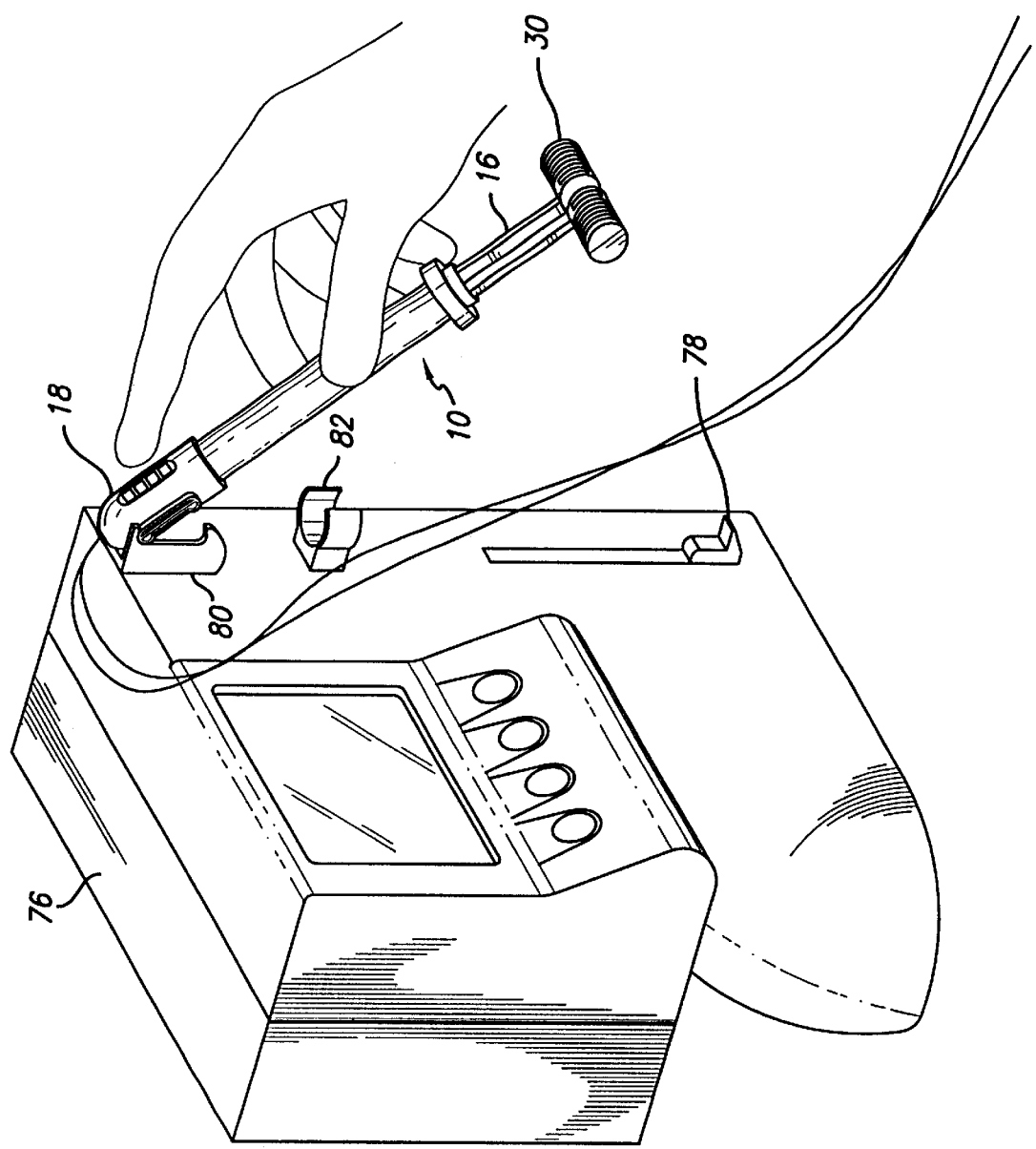
FIG. 4 is a diagrammatic view of the syringe assembly of FIG. 1 being installed into a mounting bracket, and also showing a plunger drive arm used to control the volume in the syringe.

Referring now to FIG. 4, the use of the mounting head 18 of the syringe assembly 10 of FIGS. 1 through 3 is shown. In FIG. 4, the syringe assembly 10 is being installed and mounted to an instrument 76. The instrument includes a syringe plunger drive apparatus (not shown) that has a drive arm 78 shown. The drive apparatus may be any of the well known types including a motorized lead screw using a DC motor. The drive apparatus may also be in the form of a DC servo motor, a step motor, a hydraulic motor, a pneumatic motor, or others. Whatever the specific type, the drive apparatus typically includes a moveable drive arm 78 that is capable of directing the movement of another element, such as by pushing or pulling, that it may come in contact with. The drive arm 78 as shown in FIG. 4 is in the "home" position but will move up to engage the plunger 16 of the syringe 12 for use. The syringe 12 is preferably mounted in a vertical orientation for easy detection and removal of air bubbles. Other suitable means that can pressurize or depressurize and direct a quantity of fluid may also be used.

The front of the instrument 76 in this case includes a mounting bracket 80 and a clamp 82 for holding the syringe assembly stationary in relation to the drive arm 78. In this case, the clamp 82 is an open C-type clamp with resilient arms that separate upon forcing the syringe barrel 14 through the opening between them and then reclose around the syringe barrel to capture it in place. The C-clamp 82 secures the syringe assembly 10 in position and opposes any force that may be developed by the drive arm 78 that may cause the syringe to eject from its mounting at the front of the instrument. The bracket 80 secures the syringe assembly from movement in the longitudinal, lateral, and rotational directions while the C-clamp secures the syringe assembly from movement in the normal direction. FIG. 4 shows the pivoting motion used to mount the syringe assembly 10 to the instrument 76. The mounting head 18 is first engaged with the mounting bracket 80 and the barrel 14 of the syringe is then placed into the C-clamp 82. As the mounting head 18 is placed into the bracket 80 and the syringe is pivoted into contact with the C-clamp 82, the spring-loaded electrical pins 86 come into contact with respective contact surfaces 48 on the circuit board 46.

Figure 5:
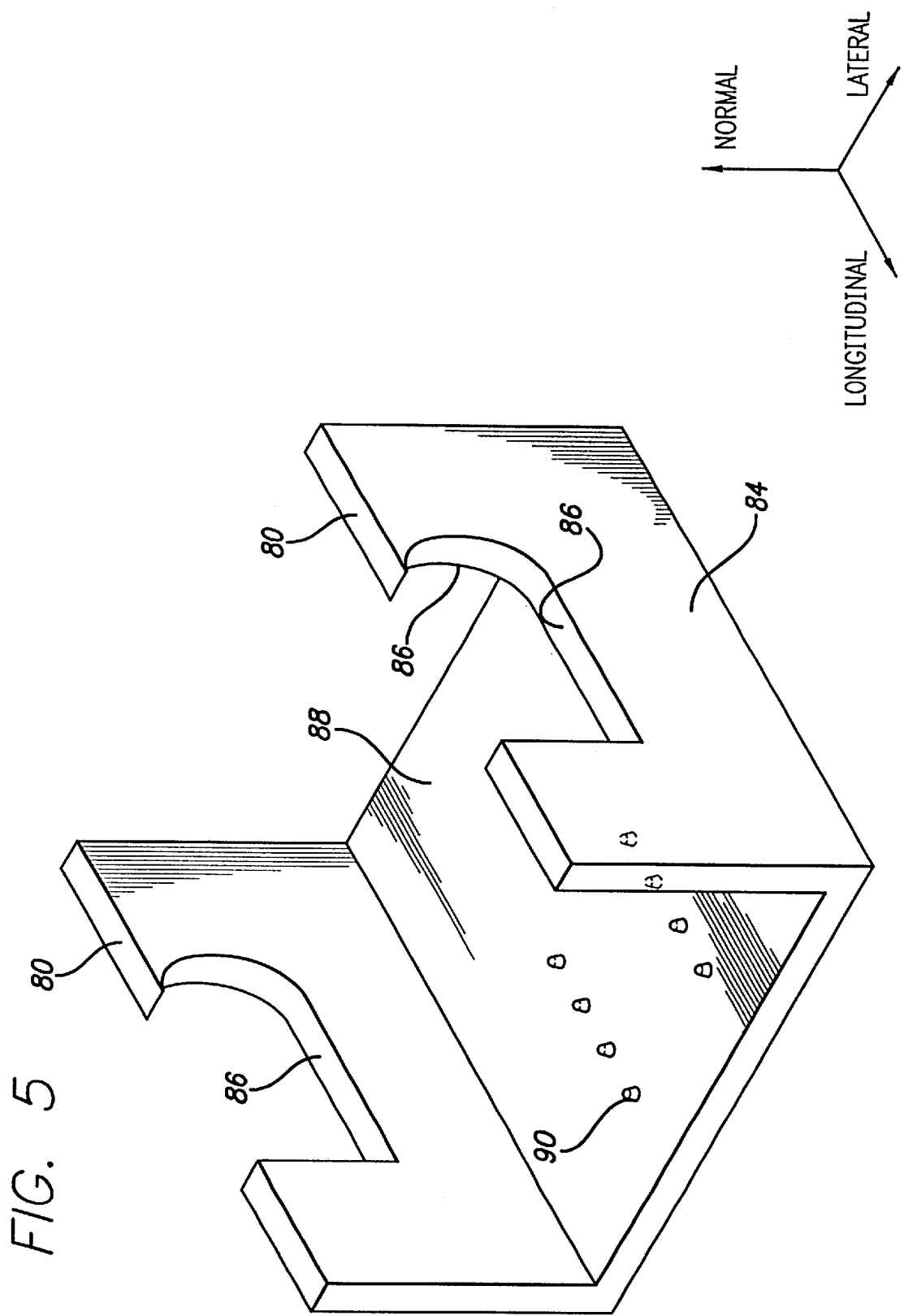
FIG. 5 is a perspective view of the mounting bracket shown in FIG. 4 for receiving the syringe assembly and showing electrical connectors for mating with the pressure sensor.

FIG. 5 shows further detail of the mounting bracket 80 that provides a pivotal connection with the mounting head 18 of the syringe assembly 10. The side walls 84 of the bracket 80 limit lateral movement of the syringe assembly 10 while the notches 86 limit movement in the longitudinal directions and limit rotational movement of the syringe assembly. Additionally, the curvature of the front end of the notch assists in limiting movement of the syringe assembly in the normal direction as does the C-clamp 82.

The base 88 of the mounting bracket 80 resides along a plane defined by the lateral and longitudinal axes. The plurality of electrical contacts 90 found on the base 88 are, in this embodiment, spring-biased electrical pins 90 that form a connection with the electrical contacts 48 of the circuit board 46 on a properly installed syringe assembly 10. As noted earlier, other means of contact engagement with the pressure sensor can be used and will be apparent to those skilled in the art. The mechanical action of the spring-biased pins 90 permits the pivotal mounting action to occur to obtain a proper mounting of the syringe assembly 10 to the instrument 76 while at the same time assuring electrical continuity with the circuit board 46. This technique for providing electrical contacts with the syringe assembly also acts as a security measure in that only a properly mounted syringe assembly will make electrical contact. The instrument 76 includes a circuit for determining if a syringe has been mounted properly and will not permit certain operations until a syringe is in place.

Additionally, the locations of the contact surfaces 48 and the pins 90 are off center from the longitudinal center line of the syringe assembly as can be clearly seen in FIG. 2. This also assists in assuring that the syringe assembly is mounted properly in that the pins will not contact the pressure sensor surfaces 48 unless the syringe is properly mounted.

Other techniques for determining if the syringe assembly has been correctly mounted may become apparent to those skilled in the art. For example, an optical system may be used that senses the presence of a tag on the syringe assembly. In another embodiment, the position of one or more of the spring-loaded pins may be monitored and when the pin or pins are moved to compress a spring, the presence of a syringe is indicated.

FIG. 6 shows a syringe assembly 10 properly installed on the instrument 76. The rounded, T-shaped handle 30 allows the operator to easily grasp the syringe assembly 10 when the need arises for removal of the syringe assembly from the instrument. As mentioned above, the pivotal mounting technique provides increased mechanical advantage in pulling the syringe barrel from the C-clamp 82. This facilitates the rapid and easy removal of the syringe assembly 10 from the instrument 76 should the need arise. When the syringe assembly is removed, the drive arm 78 is automatically moved down along the longitudinal axis to its lower limit or "home" position as shown in FIG. 4. When the drive arm reaches the home position, the instrument 76 is ready to accept the installation of the syringe assembly. The drive arm can then move forward to engage a syringe plunger.

Furthermore, as shown in FIG. 6, the syringe barrel and plunger are mounted vertically with the output of the syringe at the top. Air bubbles will rise to the top of the barrel and will be more apparent as well as easier to eliminate. Once they are at the top of the barrel, moving the plunger distally will cause them to enter the fluid line 58 where they can be purged.

Figure 7:
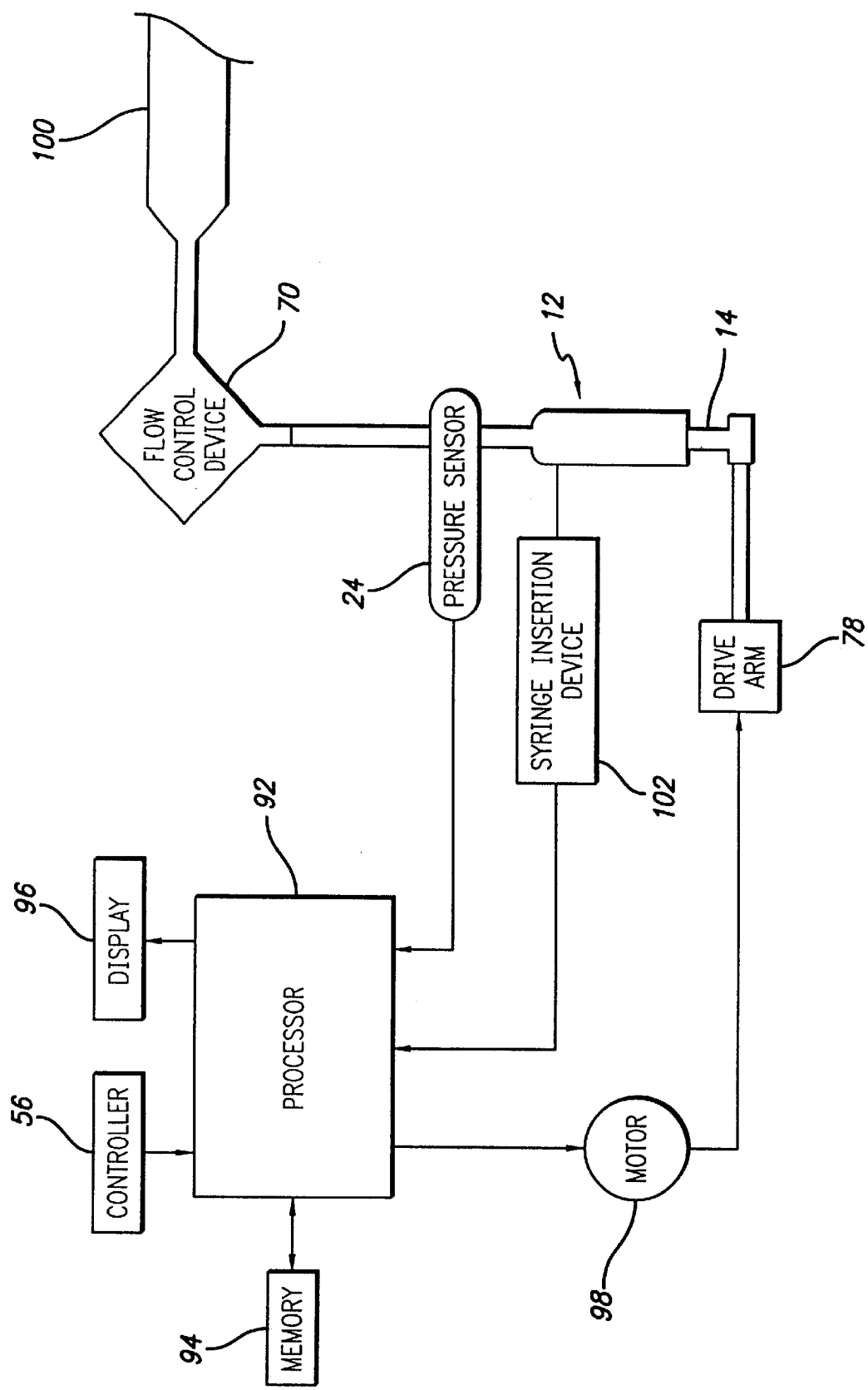
FIG. 7 is a block diagram of an automatic engagement and pressure checking system in accordance with principles of the claimed invention.

Referring now to FIG. 7, a block diagram is presented of an inflation control system. A processor 92 having a memory 94 for storing data and programs is connected to a display 96 and a controller, such as the remote controller 56 of FIG. 1. The memory 94 can take various forms such as RAM, ROM, magnetic, and others. The display 96 presents alarms as well as pressure data and other data such as the duration of each inflation, the number of inflations, and the elapsed time between inflations. Other values may be displayed as well. The controller 56 may take other forms such as front panel switches on the instrument 76 shown in FIG. 4. The processor 92 controls a motor 98 that in turn moves a drive arm 78 to move the plunger of a syringe 12. A pressure sensor 24 measures fluid pressure in the fluid line 58 and a flow control device 70, such as a stopcock, connects the fluid line 58 to a catheter 100, to a vent, or closes the line completely, as described above. A syringe insertion detector 102 is shown that detects the presence of a mounted syringe.

After mounting a syringe assembly but before the drive arm engages the syringe assembly 10, the stopcock 70 is set to the second or "vent" position, and this condition is signaled to the processor by the operator by activating a preselected switch of the remote controller 56. This allows the processor to calibrate the pressure sensor 24 to ambient atmospheric pressure. The detected pressure is then stored in memory 94 for calibrating the zero pressure value for the system. After the processor receives the confirmation signal from the preselected switch of the remote controller 56, the display 96 instructs the operator to then close the stopcock 70. Once this condition has been met, as indicated by another confirmation signal from the remote controller 56, the processor 92 then proceeds to move the drive arm 78 into engagement with the plunger 16.

Figure 8:
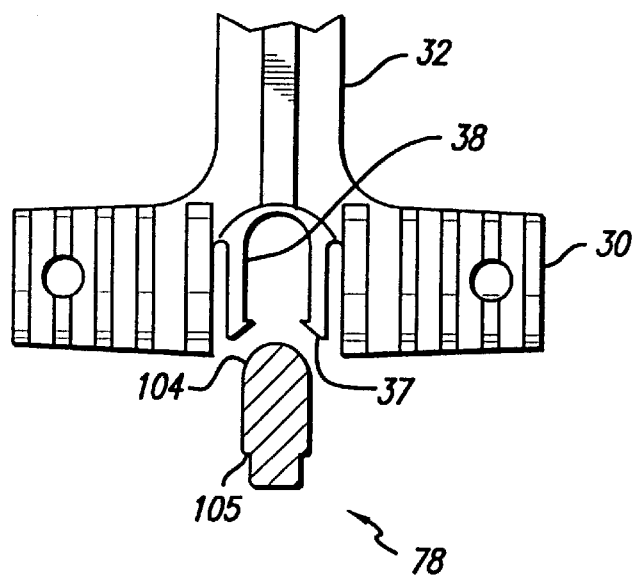
FIGS. 8, 9, and 10 are top views illustrating a sequence in which the drive arm of the syringe plunger driver apparatus engages the driver retainer of the syringe assembly.
Figure 9:
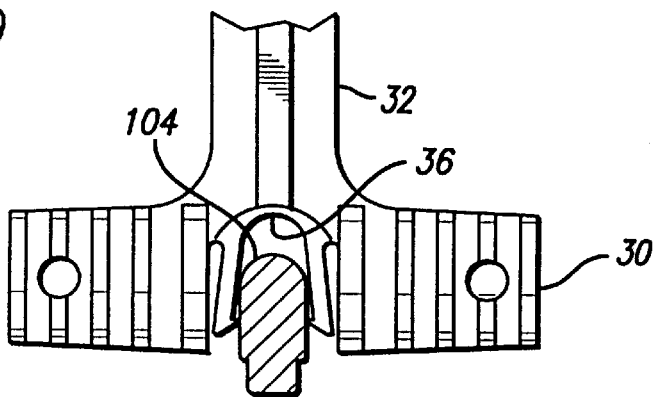
Figure 10:
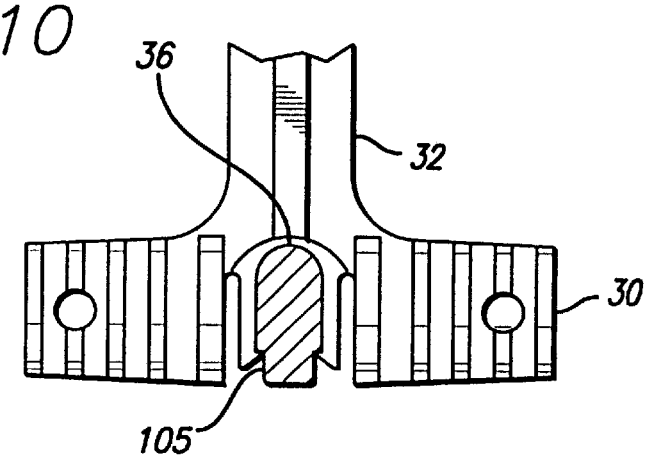

Referring now to FIGS. 8 through 10, the capture of the drive arm 78 by the drive arm retainer 36 of the syringe plunger handle 30 is illustrated. In FIG. 8, the drive arm 78 is moving forward along the longitudinal axis until it touches the barbs 38 of the prongs 37 of the retainer 36. In FIG. 9, the drive arm 78 has continued its longitudinal movement forcing the prongs and barbs apart to allow the drive arm to move between them. Upon moving completely between them as shown in FIG. 10, the prongs and barbs snap back into their at-rest position capturing the drive arm 78 between them. The barbs 38 of the driver retainer 36 have an inward slope which facilitates the movement of the rounded forward face of the drive arm 78 between them. The drive arm has a rounded front surface 104 to assist its movement past the barbs 38. Once the front portion has moved past the barbs, the barbs snap around the drive arm 78 and into notches 105 formed about half way between the rear and front surfaces for accepting the barbs of the retainer 36. The notches 105 of the drive arm 78 should be deep enough so that the barbs will capture the arm and will not allow the arm to pull out of the retainer when the arm is moving in the opposite longitudinal direction.

Additionally, the surfaces of the drive arm 78 are substantially straight and smooth in the normal direction and the surfaces of the plunger retainer 36 are straight and smooth in the normal direction so that the plunger of the syringe can rapidly be slid off the drive arm 78 by pulling it in the normal direction. Thus, the syringe handle 30 can be easily separated from the drive arm in order to facilitate easy removal of the syringe assembly 10. Manually grasping the handle 30 of the syringe assembly 10 enables the operator to manually control the pressure in the system by manually moving the plunger in the syringe. Through this means, the inflated balloon can be easily deflated by the operator manually pulling the plunger in the proximal direction.

Figure 11:
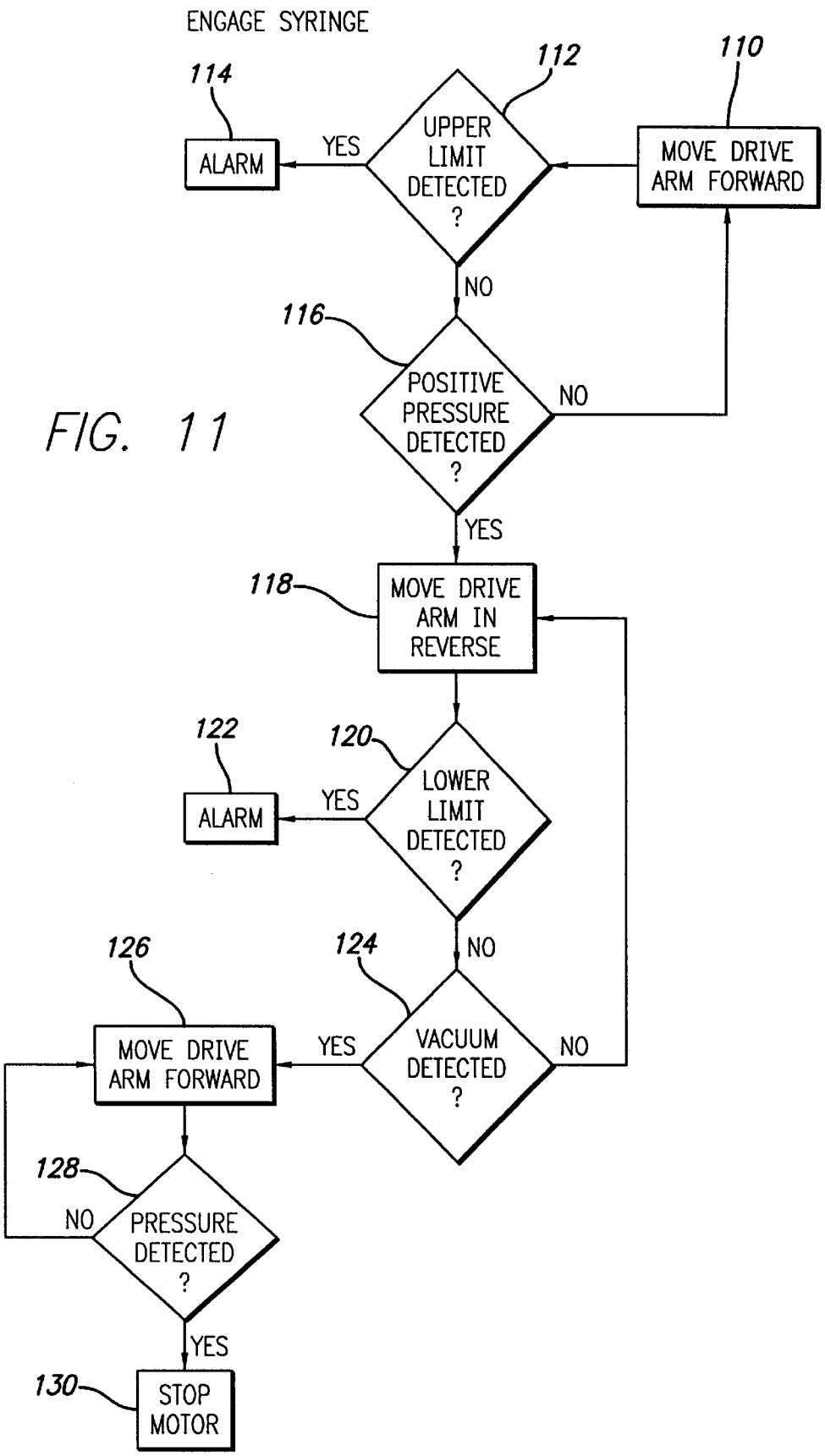
FIG. 11 is a flow chart illustrating the automatic pressure integrity testing operation of the system in accordance with principles of the claimed invention.

With the driver arm 78 engaging the driver retainer 36 of the plunger 16, the processor continues to provide command signals to move the drive arm 78 as described in the flow chart in FIG. 11. The closed stopcock 70 provides a closed system and with the pressure sensor 24, a pressure integrity test of the syringe assembly can be made.

Referring now to FIG. 11, a flow chart is presented that describes a pressure integrity test of a mounted syringe assembly. After receiving signals that a syringe is properly mounted from the syringe insertion detector 102 and that the stopcock is closed from the remote controller 56, the processor commands the motor to move the drive arm forward 110 to engage the plunger of the syringe. The processor monitors the movement of the drive arm and if it reaches its upper limit of travel before a selected amount of pressure is indicated by the pressure sensor, an alarm is declared 114. An alarm will also be declared if the motor is moving for a selected period of time and the selected amount of pressure has not yet been developed. A time-out alarm will be given.

There exist two limits of travel in this embodiment, an upper limit and a lower limit or the home position. In one embodiment, detectors are positioned at the limits and the drive arm has a flag associated with its movement. When the flag trips the respective detector, the position of the drive arm at the limit is detected.

If positive pressure is sensed 116 before the upper limit or the time-out limit is reached, the drive arm is then moved in reverse 118. The amount of positive pressure indicating that the syringe assembly has pressure integrity is selected to be higher than the pressure generated by the initial engagement process of the drive arm snapping into the plunger retainer. In one embodiment, the amount of pressure was selected to be 30 psi. If that pressure is reached, it is concluded that the syringe assembly has pressure integrity for positive pressure.

When moving in reverse, if the lower movement limit is reached by the drive arm before a partial vacuum is detected 120, an alarm is declared 122. Also, if the selected level of partial vacuum is not developed within a selected period of time, a time-out alarm is provided. However, if a partial vacuum of a selected level is sensed before the lower limit is reached 124 or the time-out limit is reached, the processor moves the drive arm forward 126 once again until slight positive pressure is sensed 128 at which time the motor is stopped 130.

In one embodiment, a negative pressure of 7 to 10 psi or approximately three-fourths atmospheres was selected as a level indicating that the syringe assembly has pressure integrity for partial vacuum. If the syringe assembly is unable to develop this amount of partial vacuum, an alarm will be provided. similarly, if the syringe assembly is unable to develop the above-mentioned positive pressure during the integrity test, an alarm is provided. Further, the instrument will not permit one to proceed with a syringe assembly unable to pass the pressure integrity test. In one embodiment, a time-out period of fifteen seconds was used for the time-out period for positive pressure and a time-out period of five seconds was used for the time-out period for partial vacuum.

At the location to which the drive arm was moved when the motor stopped, a slight positive pressure exists within the fluid line 58. When attaching a catheter to the stopcock and opening the stopcock, that slight pressure will partially inflate the balloon. This is preferable to having a negative pressure in the fluid line. If a negative pressure existed, upon opening the stopcock, air may be drawn into the fluid line, which is undesirable.

The ability to complete the routine shown in FIG. 11 means that the syringe assembly can develop both positive and negative pressures and is suitable for use in the inflation procedure. If the syringe assembly failed the test, it can be replaced at this more convenient time; i.e., before an angioplasty procedure has begun.

Figure 12:
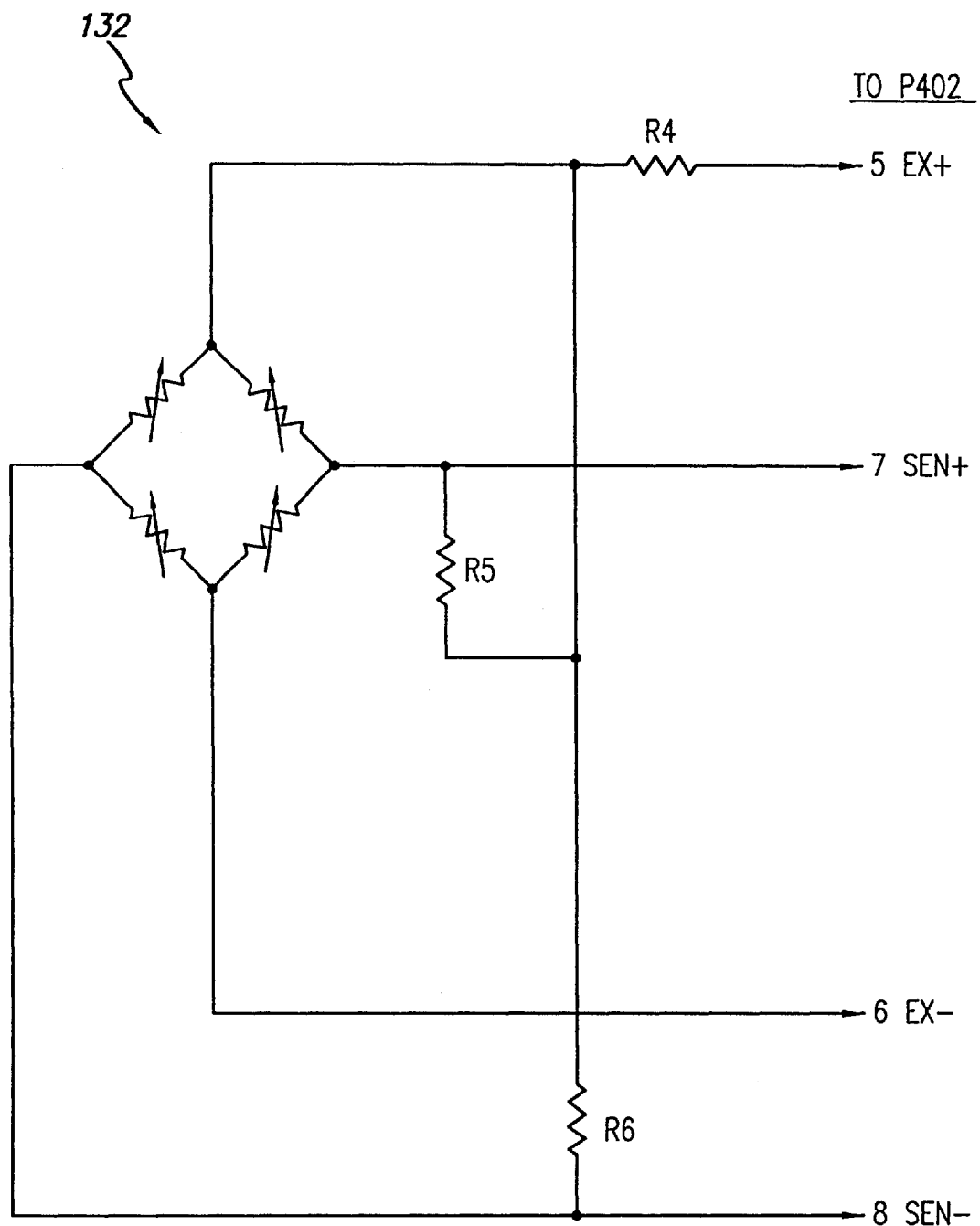
FIG. 12 presents circuitry for a pressure sensor.

A pressure sensor used in an embodiment is presented in FIG. 12 consisting of a Wheatstone bridge circuit 132 with trim resistors R4, R5, and R6. The operation of this sensor is well known to those skilled in the art.

Figure 13A:
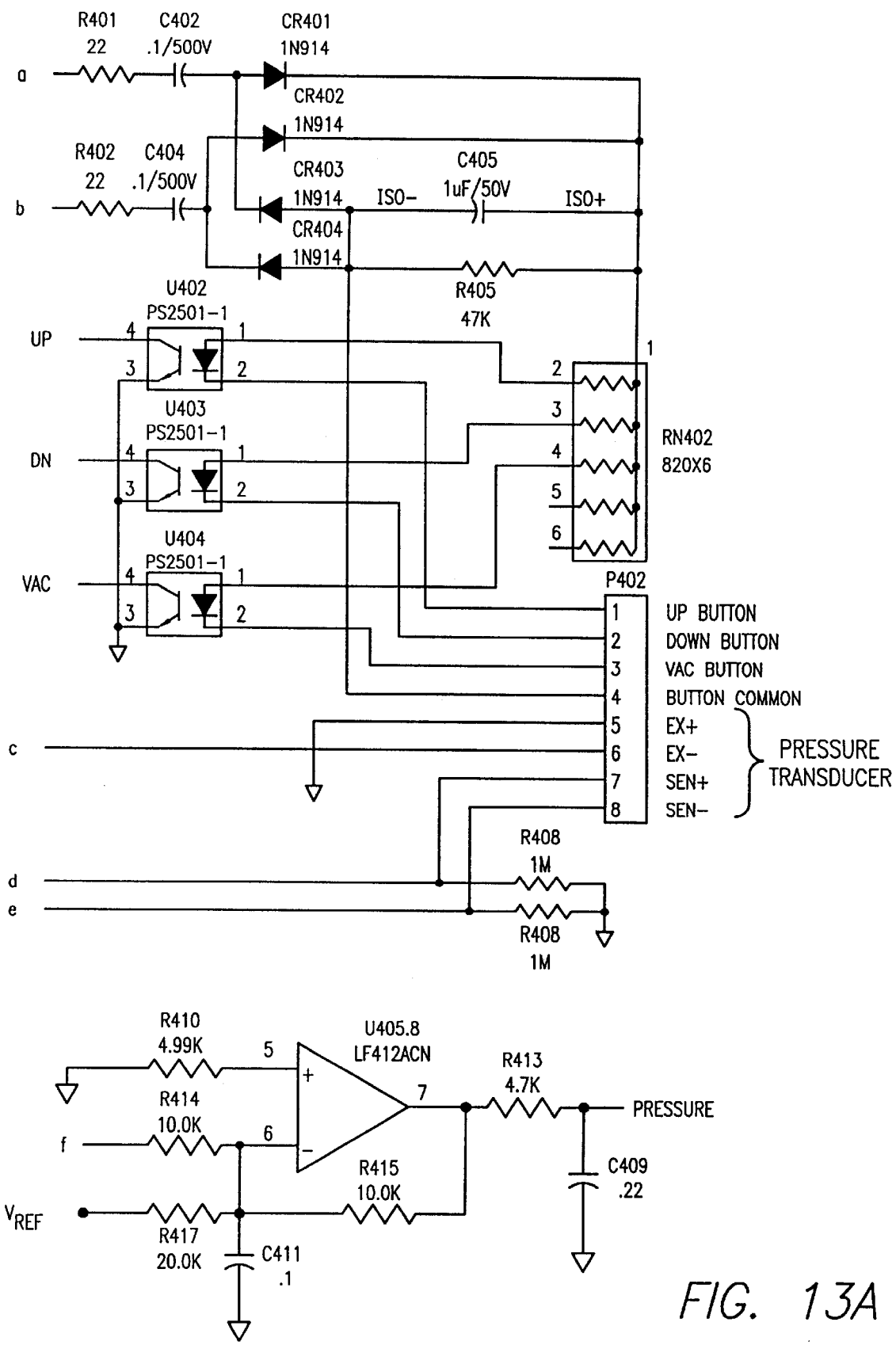
FIGS. 13A and 13B are circuit diagrams of instrument circuitry responsive to remote controller signals, pressure signals, and which provide isolation for the remote controller.
Figure 13B:
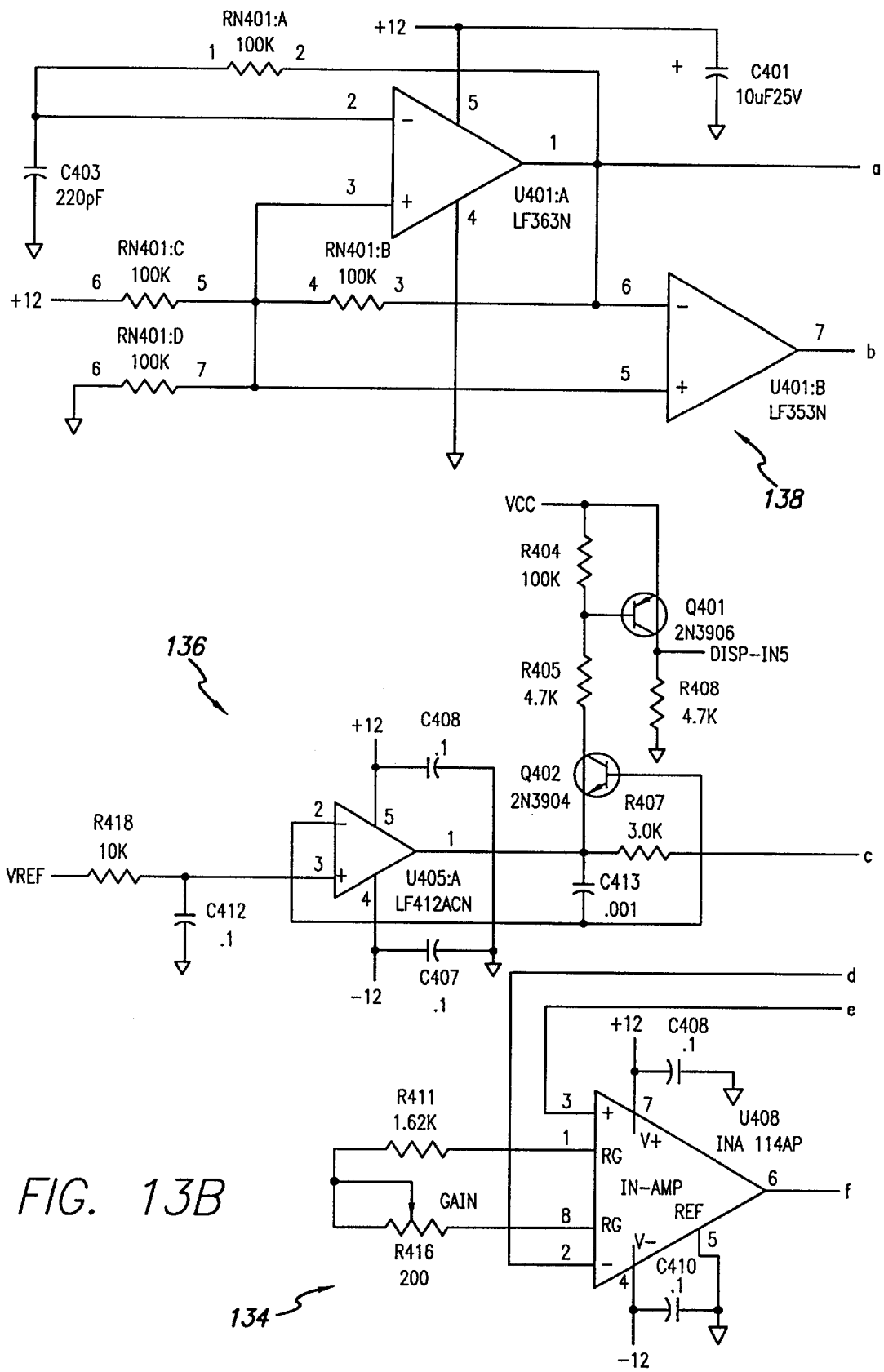

In FIGS. 13A and 13B, circuit diagrams are presented of a pressure signal processor 134 usable in the systems described above, the operation of which is apparent to those skilled in the art. An unbalance in the bridge circuit of the pressure sensor 132 causes the levels on the inverting and noninverting inputs of U405 to differ thus causing an output signal. That output signal is provided to U405-B which provides offset. A PRESSURE signal is provided for use by a processor. The level of the PRESSURE signal represents the pressure sensed by the pressure sensor 132.

To sense the existence of a syringe assembly, a syringe insertion detector 136 in the instrument is used. The position detection circuit 134 functions by detecting current across the EX+ and EX– lines. If a sensor is present, the Wheatstone bridge circuit 132 of that sensor completes the current circuit and transistor Q402 will be turned on. Transistor Q402 thus senses current flow. The device U405A controls the voltages used for the pressure sensor and transistor Q401 controls the output voltage to indicate to the processor as signal DISP-INS that a syringe is or is not present in response to transistor Q402 being turned on or off.

In the above embodiment, the Wheatstone bridge circuit forming a part of the pressure sensor mounted in the syringe assembly functions as a syringe insertion device. Its electrical connection to P402 indicates the presence of a properly mounted syringe. Other embodiments are possible, including magnetic devices and optical devices as well as different electrical circuits.

Additionally, power and isolation circuits 138 for the witches of the remote controller 56 are shown. Optical isolators U402, U403, and U404 isolate the remote controller from processor voltages. The UP, DN, and VAC signals are used by the processor as discussed above. The power circuit 106 provides a floating power source for the switches of the controller 56. The floating power circuit 106 isolates the remote controller 56 from ground and from DC sources via capacitors C402 and C404. This feature provides increased protection for persons coming in contact with the controller 56.

The LF 353N devices and the LF412ACN devices may be obtained from National Semiconductor. The INA114AP device may be obtained from Burr-Brown, and the PS205-1 devices may be obtained from NEC.

The syringe barrel is transparent to facilitate observing an air bubbles that may be trapped inside it and in one embodiment was formed of polycarbonate. The handle, shaft, and piston of the plunger was formed of ABS. The seals on the piston were formed of ethylene propylene diene monomer (EPDM). However, other materials may be used.

From the above, it is evident that the present invention provides for an advantageous design for automatically testing the pressure integrity of a syringe assembly upon installation in an inflation control system. While several particular forms of the invention have been illustrated and described, it also will be appreciated that various modifications can be made to the present invention without departing from the spirit and scope thereof.

The following pages comprise an embodiment of a computer program used to implement the above features.

© COPYRIGHT Advanced Cardiovascular Systems, Inc. 1994, 1995 All Rights Reserved Unpublished Work

What is claimed is:

1. An inflation control system comprising:
   a movable drive device having a drive arm that moves in longitudinal directions in response to drive signals;
   a syringe assembly comprising:
      a syringe barrel having a volume and a plunger opening at a proximal end and an output at a distal end;
      a fluid tube in fluid communication with the barrel volume through the output;
      a plunger movably disposed in the plunger opening and in the barrel for altering the volume by means of its position in the barrel, the plunger having a drive retainer at a proximal end, the retainer permitting the drive arm to automatically engage the retainer from one direction and after engaging, securing the plunger to the drive arm so that the plunger moves with the drive arm in longitudinal directions;
      a pressure sensor producing a signal representative of the pressure within said fluid line;
   a mounting bracket for engaging said syringe assembly and maintaining said syringe assembly in a stationary position in relation to the drive arm;
   a processor that provides drive signals to the drive device to automatically move the drive arm into engagement with the plunger retainer.

2. The inflation control system of claim 1 wherein the processor provides drive signals to the drive device to perform a syringe pressure integrity test after engagement of the drive arm with the drive retainer.

3. The inflation control system of claim 1 wherein:
   after the processor has moved the drive arm into engagement with the drive retainer, the processor controls the drive device to move the drive arm in a first longitudinal direction until a positive pressure is sensed by the pressure sensor and in a second longitudinal direction until a negative pressure is sensed by the pressure sensor.

4. The inflation control system of claim 1 further comprising:
   a flow control device that closes the fluid line;
   wherein the processor provides drive signals to the drive device to perform a syringe pressure integrity test after engagement of the drive arm with the driver retainer.
   after the processor has moved the drive arm into engagement with the driver retainer, the processor controls the drive device to move the drive arm in a first longitudinal direction until a positive pressure is sensed by the pressure sensor and in a second longitudinal direction until a negative pressure is sensed by the pressure sensor.

5. The inflation control system of claim 1 further comprising:

a flow control device that opens the fluid line;

wherein the processor receives the pressure sensor signal, compares it to a predetermined range of pressures and indicates an alarm if the sensor signal is outside that range.

6. The inflation control system of claim 1 wherein:

the driver retainer comprises two resilient retainer prongs that spread apart when initially contacted by the drive arm and which return to their at-rest positions when fully engaged by the drive arm to capture the drive arm between them.

7. The inflation control system of claim 6 wherein a notch is formed in said drive arm, and at least one of said at least two retainer prongs includes a barb for engaging said notch.

8. The inflation control system of claim 2 further comprising:

a position sensor which produces a position signal indicating when said assembly is properly mounted;

wherein the processor enables the syringe pressure integrity test only after receipt of the position signal.

9. An inflation control system comprising:

a movable drive device having a drive arm that moves in longitudinal directions in response to drive signal;

a processor that provides drive signals to the drive device to move the drive arm; and a syringe assembly comprising:

a syringe barrel having a distal end, a proximal end, and a volume, the barrel further having a plunger opening at the proximal end and an output opening at the distal end;

a plunger slidably disposed in the plunger opening and in the syringe barrel for altering the barrel volume by means of the plunger's position in the barrel, the plunger having a longitudinal axis, a distal end, and a proximal end, the plunger having a driver retainer at the plunger proximal end, wherein the driver retainer is configured to receive and automatically capture the drive arm of the movable drive device;

a fluid line in fluid communication with the barrel volume through the output opening; and a pressure sensor producing a signal representative of the pressure within said fluid line.

10. The inflation control system of claim 9, wherein the processor is configured to provide drive signals to the drive device to perform a pressure integrity test after engagement of the drive arm with the driver retainer.

11. The inflation control system of claim 10, further comprising:

a position sensor that produces a position signal indicating proper mounting of said syringe assembly;

wherein the processor enables the syringe pressure integrity test only after receipt of said position signal.

12. The inflation control system of claim 9, wherein the processor receives the pressure sensor signal, compares said pressure sensor signal to a predetermined range of pressures, and indicates an alarm if the pressure sensor signal is outside said range.

\* \* \* \* \*

UNITED STATES PATENT AND TRADEMARK OFFICE
CERTIFICATE OF CORRECTION

PATENT NO. : 6,254,569 B1
DATED : July 3, 2001
INVENTOR(S) : Joseph A. O'Donnell et al.

It is certified that error appears in the above-identified patent and that said Letters Patent is hereby corrected as shown below:

Column 12, claim 1,
Line 29, change "tube", to -- line --.

Column 12, claim 4,
Line 65, change "driver", to -- drive --.
Line 67, change "driver", to -- drive --.

Column 13, claim 6,
Line 15, change "driver", to -- drive --.

Column 13, claim 8,
Line 26, after "said", add -- syringe --.

Signed and Sealed this

Nineteenth Day of February, 2002

*Attest:*

JAMES E. ROGAN
*Attesting Officer*  *Director of the United States Patent and Trademark Office*